United States Patent [19]

Warriner

[11] Patent Number: Plant 6,795

[45] Date of Patent: May 9, 1989

[54] ROSE PLANT JACRICK

[75] Inventor: William A. Warriner, Tustin, Calif.

[73] Assignee: Jackson & Perkins Company, Medford, Oreg.

[21] Appl. No.: 85,548

[22] Filed: Aug. 14, 1987

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Majestic, Parsons, Siebert & Hsue

[57] ABSTRACT

A rose variety of the miniature class is provided having an ability to root as a softwood cutting and grow rapidly to in a four-inch pot, resistance to powdery mildew, high petal count and very few anthers.

1 Drawing Sheet

SUMMARY OF THE INVENTION

The present invention relates to a new and distinct variety of rose plant of the miniature class, which was originated by me by crossing the variety Petticoat, U.S. Plant Pat. No. 5,039, with the variety Interro, U.S. Plant Pat. No. 5,769.

The primary objective of this breeding was to produce a new rose variety of the miniature class exhibiting compact plant habit, continuously flowering, and adaptability to pot culture. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Ease of rooting as a softwood cutting;
2. Adaptability to culture as four-inch pot rose;
3. Powdery mildew resistance;
4. High petal count;
5. Glandular penduncles and petioles;
6. Very few anthers; and
7. Many petaliods.

Asexual reproduction of this new variety by softwood cutting, as performed at Irvine, Calif., shows that the foregoing characteristics and distinctions come true to form and are established and transmitted through succeeding propagation.

DESCRIPTION OF THE DRAWING

The accompanying illustration shows a typical specimen of the vegetative growth and flowers of this new variety, depicted in color as nearly true as it is reasonably possible to make the same in a color illustration of this character.

DETAILED DESCRIPTION OF THE INVENTION

The following is a detailed description of my new rose cultivar, which has been denominated "Jacrink". Color terminology is in according with The Royal Horticultural Society Colour Chart and the Pantone Matching System (1963 Edition, hereinafter "Pantone") except where an ordinary dictionary significance for the color is apparent.

Observations of the buds and flowers were made from specimens grown in a garden at Irvine, Calif. in July.

Flower

The blooming habit is continuous. The bud size is one-half inch when the petals start to unfurl. The bud form is pointed ovoid. The bud color when sepals first divide is near 192–199 (Pantone); when half blown, the upper side of petals is near 192–199 (Pantone) to Red 49B and the lower side of petals is near 192–199 (Pantone). The sepals have a color near Green Group 138B to Green Group 138C. The surface texture is covered with fine hairs. There are three appendaged sepals normally appendaged, and two unappendaged sepals with a hairy edge. The receptacle color is medium green, of a funnel shape, small size and smooth surface. The peduncle is of medium length, and glandular surface. Peduncle color is medium green and the penduncle is stiff and erect.

Bloom

Bloom size is small, with an average open size of one and one-fourth inches, borne singly and several together in clusters. The clusters are rounded. The stems are strong and short. The form when first open is cupped. This form then flattens and the outer petals curl back, quill fashion. Under normal conditions there are 55 to 60 petals. The upper side of petals is near Red Group 42A, as is the reverse side of the petals. The base of petals has a small cream-colored half moon at the point of attachment, and the major color is near 192–199 (Pantone) fading to Red Group 52A to 52C. There are occasional white streaks on the outer petals. The general tonality at the end of the first day shows no change in color. At the end of the third day, there is general fading to a pink color near Red Group 52A to 52C.

The fragrance is slight. The petal texture is thick, of a round shape with the tips being flat and slightly recurved and edges moderately quilled.

The arrangement is imbricated with many small petaloids in the center. The blooms drop off cleanly, and last on the plant for a long period of time on the plant.

Reproductive Parts

The anthers are small and few to none, of yellow color, regular around styles and mixed with petaloids. The filaments are white, the pollen is lemon yellow, the style are white, and the stigmas are red.

Plant

A miniature bush of vigorous dwarf and compact growth habit.

Foliage

Small size, normal in quality. The new foliage is reddish bronze, and the old foliage is dark green. Normal mid-stem leaves have five leaflets.

The leaflets are of an oval pointed shape, are smooth in texture, and have a serrated edge. The serration is single and small in size. Petiole rachis is green and petiole underside is rough with prickles, edges with glands. Stipules are medium and serrated. The foliage is resistant to mildew under normal growing conditions at Irvine, Calif.

Wood

New wood is light green, with a smooth bark. Old wood is green with a smooth bark.

Prickles

There are a few prinkles on a main canes from the base and on laterals from the main canes. The form is short and straight. Color when young is transparent.

Small Prickles

There are no small prickles on the main stalks or on the laterals.

Additional Distinguishing Traits

This novel rose plant is very adaptable to culture in four-inch pots, as its roots readily form softwood cuttings and flowers within five to six weeks from a pinch.

Parentage

The seed parent is Petticoat, U.S. Plant Pat. No. 5,039. The pollen parent was Interro, U.S. Plant Pat. No. 5,769.

Classification

Botanical is rosa hybrid and commercial is miniature.

I claim:

1. A new and distinct variety of rose plant and parts thereof of the miniature class substantially as herein shown and described, characterized particularly as to novelty by a compact growth habit, an ability to root readily as a softwood cutting and adaptability to production as a four-inch pot plant, high petal count, presence of glands on the peduncle and petioles, very few anthers, many petaloids and resistance to powdery mildew.

* * * * *

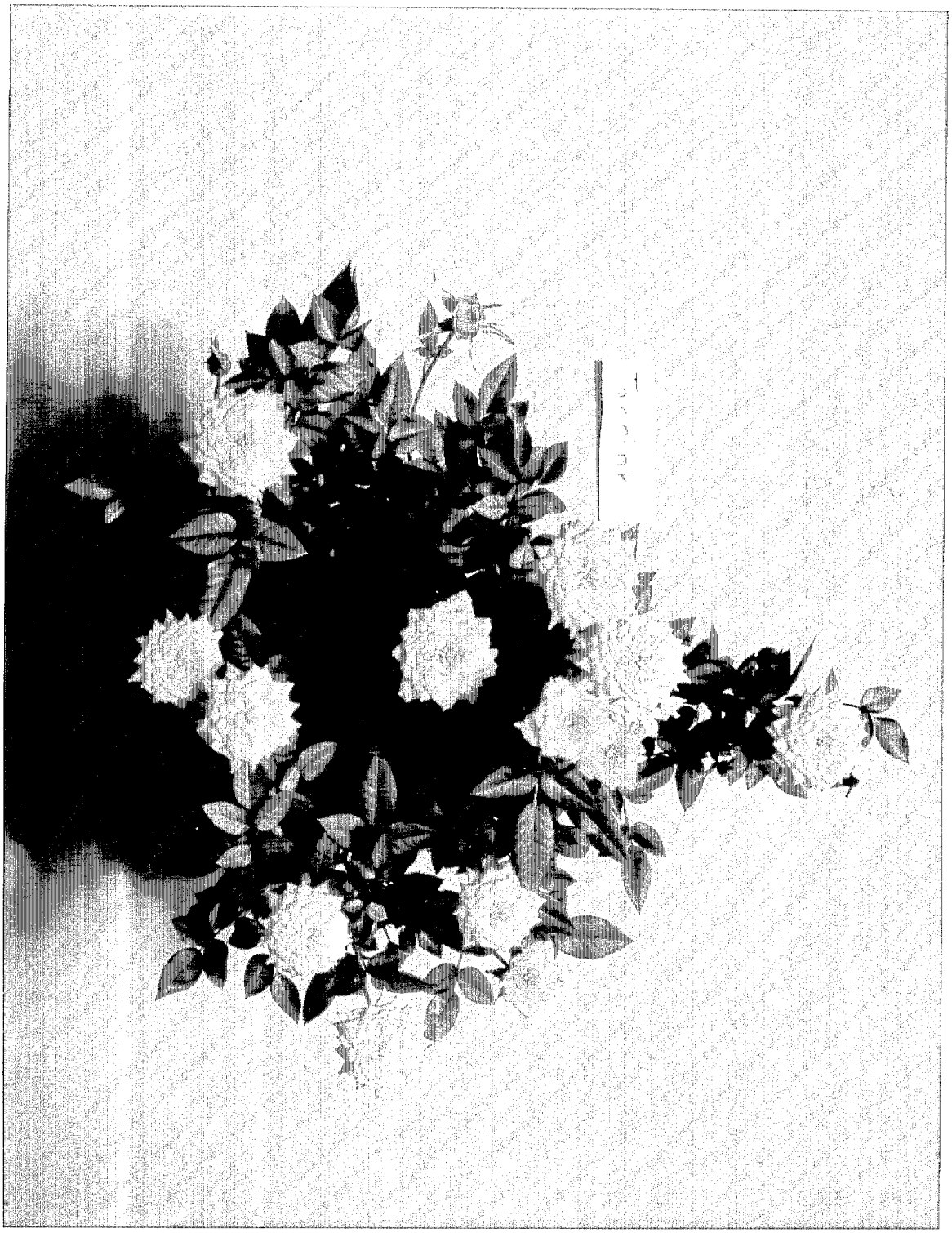

UNITED STATES PATENT AND TRADEMARK OFFICE

CERTIFICATE OF CORRECTION

PATENT NO. : Plant 6,795

DATED : May 9, 1989

INVENTOR(S) : Warriner

It is certified that error appears in the above-identified patent and that said Letters Patent is hereby corrected as shown below:

In the Title, replace "JACRICK" with —JACRINK--;

Col. 2, line 49, "style" should be --styles--; and

Col. 3, line 26, delete "a" between "on" and "main".

Signed and Sealed this

Twenty-first Day of November, 1989

*Attest:*

JEFFREY M. SAMUELS

*Attesting Officer* *Acting Commissioner of Patents and Trademarks*